United States Patent [19]
Ellis, Jr.

[11] Patent Number: 5,149,507
[45] Date of Patent: Sep. 22, 1992

[54] METHOD OF VENTING A STERILIZER
[75] Inventor: Charles E. Ellis, Jr., Phelps, N.Y.
[73] Assignee: MDT Corporation, Torrance, Calif.
[21] Appl. No.: 648,239
[22] Filed: Jan. 31, 1991
[51] Int. Cl.5 .................. A61L 2/00; G05D 16/00
[52] U.S. Cl. ................................. 422/112; 422/26; 422/33; 422/114; 422/113; 422/295
[58] Field of Search ............... 422/26, 33, 112, 113, 422/295, 114

[56] References Cited
U.S. PATENT DOCUMENTS

| | | | |
|---|---|---|---|
| 3,088,180 | 5/1963 | Lauterbach | 422/25 |
| 3,246,947 | 4/1966 | Castle | 422/26 |
| 4,309,381 | 1/1982 | Chamberlain et al. | 422/3 |
| 4,759,909 | 7/1988 | Joslyn | 422/26 |
| 4,781,898 | 11/1988 | Jones | 422/295 |
| 4,971,764 | 11/1990 | Albright | 422/110 |

Primary Examiner—Robert J. Warden
Assistant Examiner—T. A. Trembley
Attorney, Agent, or Firm—Trask, Britt & Rossa

[57] ABSTRACT

The application is directed to methods and apparatus for venting a pressurized sterilizer chamber having a liquid load within it. A sterilizer chamber is provided with a pressure sensor for sensing the chamber pressure and a vent channel with an associated vent valve. The vent valve is opened to vent pressure from the chamber, and has an orifice providing a maximum flow coefficient substantially larger than a standard bleed valve. A microprocessor-based sterilizer controller monitors chamber pressure and opens and closes the vent valve. The venting phase is regulated by means of a series of vent cycles. An individual vent cycle is intiated by starting a software timer to time a preset interval. The controller records a starting chamber pressure and opens the vent valve. The controller monitors the chamber pressure, and when the pressure has dropped from the starting pressure by a selected maximum amount, closes the vent valve until the timer interval has elapsed. If the maximum pressure drop is not achieved in the given interval, the vent valve remains open as the next vent cycle is started.

16 Claims, 3 Drawing Sheets

METHOD OF VENTING A STERILIZER

BACKGROUND OF THE INVENTION

1. Field

The invention relates to pressurized sterilizers, and more particularly to means for venting the chamber of such a sterilizer.

2. State of the Art

Apparatus for sterilization by pressurized vapor in a pressure chamber is well known. Both dry articles and liquids can be sterilized in such chambers. After a pressure cycle is complete, the chamber must be depressurized or vented to facilitate opening of the chamber door for removal of the load and to prevent injury to the operator. It is desirable to vent the load as quickly as possible so that the goods are available more quickly and sterilizing cycles can be performed more rapidly. However, where the load comprises sterilized liquids, a too-rapid drop in chamber pressure will cause some of the liquid to boil off and be lost. Losses of more than about 5% of liquid volume are considered unacceptable. Thus, it is important that the rate of pressure drop during venting of a liquid load remain below the rate at which significant liquid boil-off occurs.

One previous method of venting is to open a bleed valve having a relatively small orifice, so that the pressure drops at a slow rate. Venting in this manner is rapid at first, but slows considerably as the pressure drops, so that the venting time is relatively long.

An improvement described in U.S. Pat. No. 4,781,898 to Jones, provides two vent paths. The first vent path is a slow bleed valve Which directs the steam into a condensing coil. The second path is activated when the chamber pressure has dropped below a predetermined level, and vents rapidly and directly to the atmosphere. However, while provision of the second path speeds up the venting process, it does not control the rate of venting in the early stage. Moreover, this two-channel venting requires extra plumbing and space and is accordingly more expensive.

Another venting method is described in U.S. Pat. No. 4,971,764 to Albright. In this method, an orifice having a relatively large flow coefficient is used. A sterilizer control governs opening and closing of the orifice according to duty cycles based on the detected rate of pressure and/or temperature drop within the chamber, thereby varying the effective flow coefficient. The duty cycle is repeatedly re-calculated to keep the rate of venting constant. However, the implementation of this method is relatively complicated and expensive. Errors can arise in calculation of the duty cycles. Also, the control of the duty cycle in progress is not responsive to the rate of pressure drop occurring during that duty cycle.

Consequently, a need remains for simple means to vent a liquid load at a controlled rate which keeps liquid loss within a desired range, while still providing a rapid vent cycle.

SUMMARY OF THE INVENTION

The invention is directed to methods and apparatus for venting a pressurized sterilizer chamber having a liquid load within it. A sterilizer chamber is provided with a pressure sensor disposed for sensing the chamber pressure, and a vent channel with an associated vent valve. The vent valve is openable to vent pressure from the chamber, and has an orifice providing a maximum flow coefficient substantially larger than a standard bleed valve. Microprocessor-based sterilizer control means is connected to the pressure sensor to monitor chamber pressure, and to the vent valve to open and close the valve. The sterilizer control means includes a timer which functions to time a preset interval.

The sterilizer control means is operable to control a venting phase by means of a series of vent cycles. An individual vent cycle is initiated by starting the timer to time the preset interval. A starting chamber pressure is recorded by the control means from the pressure sensor, and the vent valve is opened. The control means continues monitoring the pressure sensed by the sensor, and compares it to the starting pressure. When the sensed chamber pressure has dropped from the starting pressure by a selected maximum amount, the control means closes the vent valve until the timer interval has elapsed. If the maximum pressure drop is not achieved in the given interval, the vent valve remains open as the next vent cycle is started. In this manner, the maximum pressure drop in a specified interval is limited during the early stage of venting. Towards the end of the venting cycle, the control means leaves the valve open substantially continually, so that the cycle is completed as rapidly as possible.

DETAILED DESCRIPTION OF THE ILLUSTRATED EMBODIMENT

Figure 1:
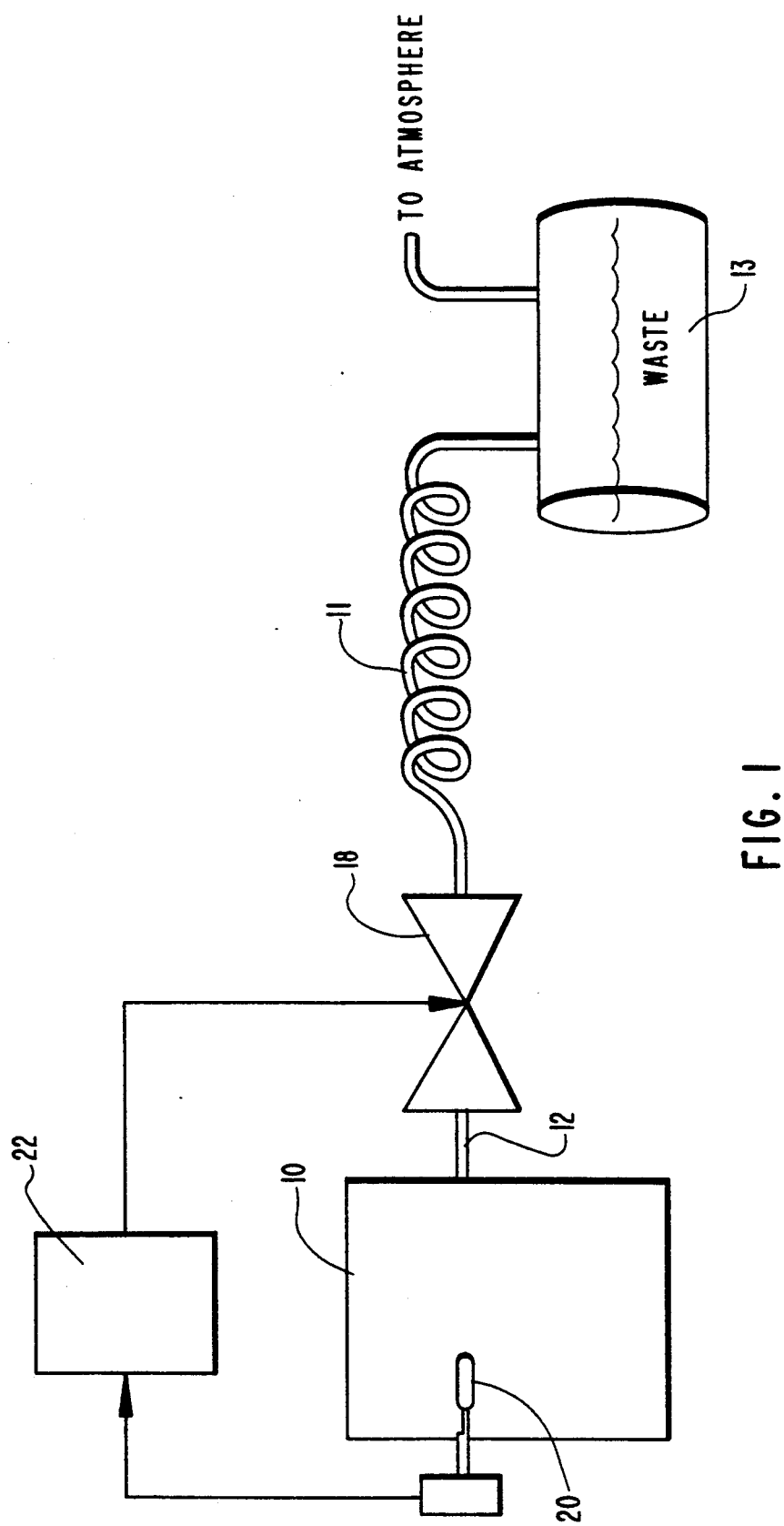
FIG. 1 is a simplified diagram of a sterilizer with venting controlled as described herein.

As shown by FIG. 1, a pressurizable sterilizing chamber 10 has a vent channel 12 which is connected to atmosphere via condensing coils 11 and a waste reservoir 13. Vent channel 12 includes a valve 18 which when opened, allows steam and liquid from chamber 10 to escape to atmosphere. In the illustrated embodiment, valve 18 is a solenoid-operated valve. Optionally, vent channel 12 also includes condensing coils 11 and a waste reservoir 13. A pressure sensor 20 is disposed for sensing the pressure within chamber 10. Pressure sensor 20 is operably connected to send pressure signals reflective of the sensed pressure to sterilizer control means 22.

Sterilizer control means 22 is associated with valve 18 for controlling the venting of the chamber. Control means 22 is a microprocessor-based sterilizer control which may be programmed in a conventional way to control temperature and pressurization of sterilizer chamber 10. Control means 22 is connected to pressure sensor 20 to receive pressure data reflecting the pressure sensed within the chamber. Control means 22 is also connected to vent valve 18 to control its opening and closing. As is conventional in the art of sterilizer controls, control means 22 includes a timer for timing various intervals as required during control of a sterilization cycle. Control means 22 thus is operable to time preset intervals during the venting phase.

The orifice of valve 18 should be substantially larger than a typical bleed valve. A typical bleed valve may have an orifice of diameter about 0.0625". However, valve 18 should have an orifice of at least about tenfold greater diameter than such a bleed valve. In the illustrated embodiment, valve 18 has an orifice of about 3/32".

Figure 2:
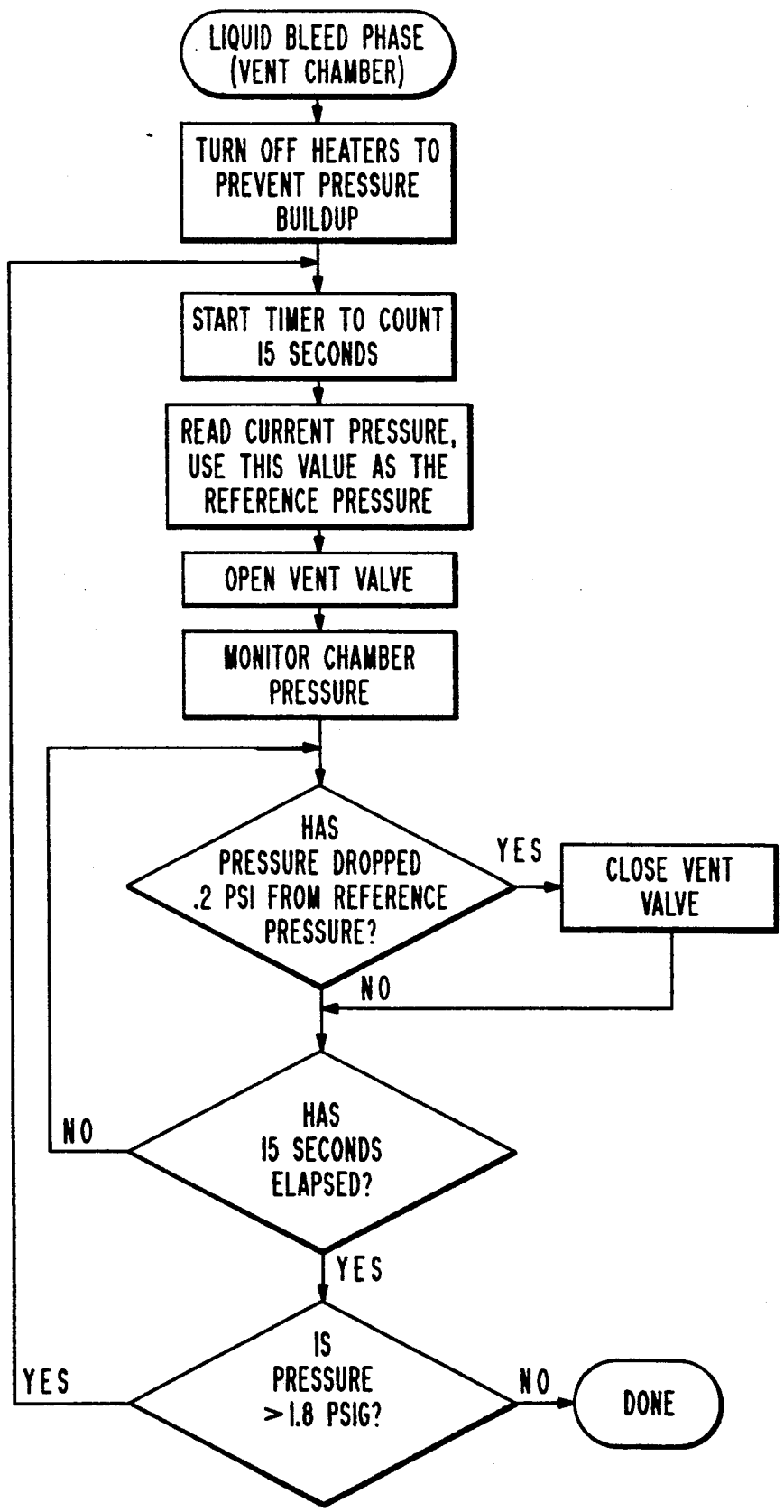
FIG. 2 is a logic flow diagram describing the operation of a working example of the sterilizer control means and method of this invention.

Controller 22 is operable to control the venting phase according to a series of vent cycles described by the flow chart of FIG. 2. The vent cycles are of equal preset time periods. In each vent cycle, at the start of the cycle control means 22 reads and stores the starting (or reference) pressure in the chamber, starts the timer to time a preset interval, and opens vent valve 18. During the preset interval, controller 22 monitors the pressure signals received from sensor 20 and detects whether the chamber pressure has dropped by a preselected maximum amount from the reference pressure. If it has, controller 22 sends a signal to close valve 18. If not, the valve stays open.

In either case, controller 22 then detects whether the preset interval has elapsed. If it has not, controller 22 continues to compare pressure readings from sensor 20 to the reference pressure until either the maximum pressure drop is reached, or the preset interval elapses. When the interval has elapsed, and if the chamber pressure remains greater than atmospheric, a new vent cycle is initiated. A new reference pressure is read, the timer is started to count another interval, and valve 18 is opened. The vent cycles are thus repeated until the chamber reaches approximately atmospheric pressure.

The maximum permissible rate of pressure drop within the chamber is determined by the length of the counter interval in combination with the maximum allowed pressure drop per interval. Pressure drop rates of 1 psi per minute or less limit the losses from a liquid load to about 3% or less. In a preferred embodiment, the rate of pressure drop within the chamber is limited to about 0.8 psi per minute. The timer interval should be short, ideally less than about one minute, to ensure that the chamber pressure doesn't drop by too much within a single interval.

In a preferred embodiment, the time interval is about 15 seconds, however, smaller intervals are within contemplation. To maintain with a pressure drop rate of 0.8 psi per minute, the maximum allowed pressure drop within one 15 second interval is about 0.2 psi. However, other combinations of interval length and maximum pressure drop per interval may be used, so long as the overall rate of pressure drop within the chamber is not more than about 1 psi per minute.

Figure 3:
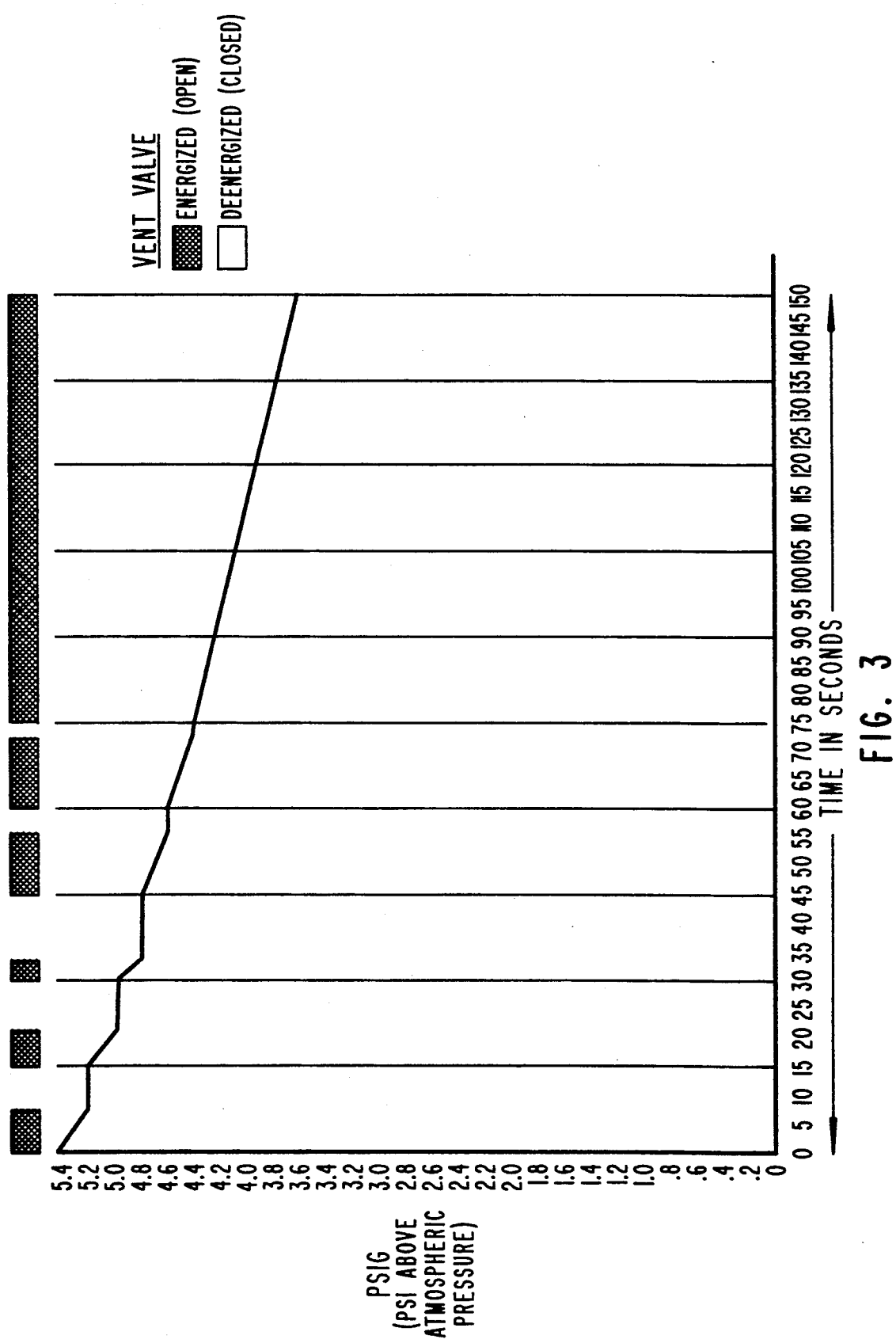
FIG. 3 is a simulated chart of pressure vs. time during a venting cycle illustrating the method of venting.

FIG. 3 comprises a simulated pressure drop curve illustrating the effect of the venting cycles of FIG. 2. The bar chart along the top of FIG. 3 indicates the portion of each interval during which valve 18 is open. As can be seen, valve 18 remains open for nearly the entire period during which the last few pounds of excess chamber pressure are vented.

A test of venting of a liquid load was made using the embodiment having a maximum pressure drop of 0.2 psi per 15 second interval. From a starting pressure of 25 psi above atmospheric, about 30 minutes was required to vent down to atmospheric pressure. The average rate of chamber pressure drop was about 0.7 to 0.8 psi per minute. From a starting volume of 1000 ml of water per flask, an average of about 25 ml per flask was lost, or about 2.5%.

A method of controlled venting of a sterilizer may be performed as follows. A vent cycle is initiated by approximately simultaneously recording a reference pressure, starting a timer to time a preset interval, and opening the vent valve. The pressure sensor is monitored and the pressure data are compared to the reference pressure. When the difference between the reference pressure and the current chamber pressure reaches a selected maximum level, the vent valve is closed until the counter finishes counting the interval. The next vent cycle is then initiated. The process is repeated until the chamber reaches approximately atmospheric pressure. The preselected interval should be between about 10 seconds and 1 minute, with the preferred interval being about 15 seconds. The maximum pressure drop within an interval is selected to correspond to a rate of pressure drop of no more than 1 psi per minute, and preferably about 0.8 psi per minute.

The method and control apparatus described hereinabove limit boil-off losses from a liquid load to about 3% or less. At the same time, the venting rate at the end of the cycle is substantially maximized (for a given vent orifice) and consequently the venting time is shortened. The method is inexpensive to implement, requires no extra plumbing and avoids errors which may arise in complicated calculations of duty cycles. Moreover, the apparatus and method are immediately responsive to a sensed pressure drop to close the vent valve, thereby absolutely limiting the maximum pressure drop within an interval.

While the invention is described with reference to particular embodiments, it is understood that it is not limited to the specific details of these embodiments. The claims themselves define the scope of the invention.

What is claimed is:

1. A method of venting a sterilizer chamber comprising the steps of:
   providing a sterilizer chamber containing a liquid load at elevated pressure;
   providing sensing means disposed for sensing the pressure within said sterilizer chamber;
   providing valve means for selectively opening and closing a vent associated with said sterilizer chamber;
   providing timing means for timing a series of venting intervals of selected duration, each of the venting intervals having a start and an end;
   opening said valve means to vent the sterilizer chamber;
   starting the timing means to time a venting interval;
   monitoring the pressure sensed by the sensing means;
   closing the valve means if a drop in said pressure which exceeds a preselected maximum drop occurs between the start and end of the venting interval, and, if the valve means has been closed, reopening the valve means at the end of the venting interval; and
   repeating in sequence said steps of starting the timing means, monitoring the pressure, and closing and reopening the valve means until the pressure within the sterilizer chamber is below a desired level.

2. The method of claim 1, wherein said step of monitoring further includes the steps of:
   reading a starting pressure from said sensing means at the start of the venting interval;
   taking a plurality of subsequent pressure readings at a series of times during the venting interval; and
   determining the decrease in pressure since the start point represented by each of the subsequent pressure readings.

3. The method of claim 1, wherein the venting interval is at least about one minute and the preselected maximum drop is about 1 psi.

4. The method of claim 3, wherein the venting interval is at least about fifteen seconds and the preselected maximum drop is about 0.2 psi.

5. In a sterilizer of the kind having a pressurizable chamber for sterilizing liquids, pressure sensing means disposed for sensing pressure within said pressurizable chamber, vent valve means operably associated with said pressurizable chamber for venting pressure, and control means operably associated with said pressurizable chamber for controlling sterilizing cycles, the improvement comprising:

said control means including timing means for timing intervals, and venting control means communicatively connected to said timing means, said pressure sensing means and said vent valve means, and constructed to:

open said vent valve means to vent said pressurizable chamber, activate said timing means to time a venting interval having a present duration defined by a start and an end;

monitor the pressure sensed by said pressure sensing means during said venting interval;

close said vent valve means if the amount of pressure decrease within said venting interval exceeds a preselected limit and reopen said vent valve means at the end of said venting interval.

6. The improvement of claim 5, wherein said venting control means is further constructed to repetitively activate said timing means, monitor said pressure, and close and reopen said valve means until said pressure is at or below a desired level.

7. The improvement of claim 5, wherein said venting control means is further constructed to:

read a starting pressure from said pressure sensing means at the start of said venting interval; and read subsequent pressures at a series of subsequent times within said venting interval;

subtract each individual said subsequent pressure from said starting pressure to calculate a decrease in chamber pressure at each of said subsequent times; and to determine whether said decrease exceeds said preselected limit.

8. The improvement of claim 7, wherein said venting control means controls said preselected limit to be equal to or less than about 1 psi and said preset interval to be at least about one minute.

9. The improvement of claim 8, wherein said venting control means controls said preselected limit to be equal to or less than about 0.2 psi and said preset interval to be at least about 15 seconds.

10. A sterilizing apparatus, comprising:

a pressurizable chamber for sterilizing;

sensing means disposed for sensing pressure within said pressurizable chamber;

venting means mechanically adapted to said pressurizable chamber for venting pressure from said pressurizable chamber;

control means operably associated with said venting means and communicatively connected to receive pressure data from said sensing means for controlling the venting of said pressurizable chamber by said venting means, said control means including timing means for timing a venting interval of preset duration, and further being constructed to:

signal said venting means to begin venting said pressurizable chamber;

signal said timing means to start timing said venting interval as soon as said venting means has begun venting said pressurizable chamber;

monitor a plurality of pressure readings received from said sensing means during said venting interval;

determine a decrease in chamber pressure occurring during said venting interval from each of said pressure readings; and to signal said venting means to cease venting said pressurizable chamber when said decrease exceeds a preselected limit, and signal said venting means to begin venting again as soon as said venting interval has elapsed.

11. The apparatus of claim 10, wherein said venting means includes a vent valve operably connected to said control means to receive and implement signals to open to vent said chamber and to close to cease venting said chamber, and wherein said control means is further constructed to repetitively signal said timing means to start timing, monitor a plurality of pressure readings, determine a decrease in chamber pressure, and signal said venting means to cease venting and to begin venting again, until said pressure is at or below a desired level.

12. The apparatus of claim 11, wherein said interval of preset duration is at least about one minute, and said control means is further constructed to maintain said preselected limit at a value equal to or less than about 1 psi.

13. The apparatus of claim 12, wherein said interval of preset duration is at least about 15 seconds, and said control means is further constructed to maintain said preselected limit at a value equal to or less than about 0.2 psi.

14. In a method of venting a sterilizer chamber containing a liquid load and having a vent for venting the sterilizer chamber, the improvement comprising limiting the rate of venting the sterilizer chamber by:

providing sensing means disposed for sensing the pressure within said sterilizer chamber;

providing valve means for selectively opening and closing the vent associated with the sterilizer chamber;

providing timing means for timing a venting interval of preset duration, the venting interval having a start and an end;

opening the valve means to vent the sterilizer chamber;

activating the timing means to time the venting interval;

monitoring the pressure sensed by the sensing means;

determining a decrease in sterilizer chamber pressure occurring since the start of the venting interval;

closing the valve means if and when the decrease in sterilizer chamber pressure occurring prior to the end point of the venting interval reaches a preselected maximum amount, and, when the valve means has been closed, reopening the valve means after the end of the venting interval; and repeating said steps of activating the timing means, monitoring the pressure, determining the pressure decrease, and closing and reopening the valve means, until the pressure within the sterilizer chamber is below a desired level.

15. The method of claim 14, wherein the venting interval is at least about one minute and the preselected maximum drop is about 1 psi.

16. The method of claim 15, wherein the venting interval is at least about fifteen seconds and the preselected maximum drop is about 0.2 psi.

* * * * *